(12) United States Patent
Tsao et al.

(10) Patent No.: US 11,564,757 B2
(45) Date of Patent: Jan. 31, 2023

(54) LASER-ASSISTED SURGICAL ALIGNMENT

(71) Applicant: THE REGENTS OF THE UNIVERSITY OF CALIFORNIA, Oakland, CA (US)

(72) Inventors: Tsu-Chin Tsao, Los Angeles, CA (US); Cheng-Wei Chen, Los Angeles, CA (US); Yu-Hsiu Lee, Los Angeles, CA (US); Matthew Gerber, Los Angeles, CA (US); Jean-Pierre Hubschman, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 286 days.

(21) Appl. No.: 16/487,074

(22) PCT Filed: Feb. 26, 2018

(86) PCT No.: PCT/US2018/019760
§ 371 (c)(1),
(2) Date: Aug. 19, 2019

(87) PCT Pub. No.: WO2018/157078
PCT Pub. Date: Aug. 30, 2018

(65) Prior Publication Data
US 2019/0380795 A1    Dec. 19, 2019

Related U.S. Application Data

(60) Provisional application No. 62/464,297, filed on Feb. 27, 2017.

(51) Int. Cl.
*A61B 90/13* (2016.01)
*A61B 90/50* (2016.01)
(Continued)

(52) U.S. Cl.
CPC .............. *A61B 34/30* (2016.02); *A61B 90/13* (2016.02); *A61B 90/50* (2016.02); *A61B 34/20* (2016.02);
(Continued)

(58) Field of Classification Search
CPC .......... A61F 9/00736; A61F 2090/0035; A61F 2090/3937; A61F 2090/064;
(Continued)

(56) References Cited

U.S. PATENT DOCUMENTS 5,143,076 A * 9/1992 Hardy .................. A61N 5/1031
600/407
5,387,220 A * 2/1995 Pisharodi ............... A61B 90/14
128/898
(Continued)

OTHER PUBLICATIONS

International Preliminary Report on Patentability issued in PCT Application No. PCT/US2018/019760 dated Sep. 6, 2019, 6 pages.
(Continued)

*Primary Examiner* — Jocelin C Tanner
(74) *Attorney, Agent, or Firm* — Foley & Lardner LLP

(57) ABSTRACT

A robotic surgery system includes: (1) a positioning stage and (2) at least one manipulator arm mounted to the positioning stage, wherein the manipulator arm includes a track
(Continued)

and a tool carriage moveably mounted to the track, and the tool carriage includes a base and a pair of light emitting devices mounted to the base.

15 Claims, 5 Drawing Sheets

(51) Int. Cl.
*A61B 90/14* (2016.01)
*A61F 9/007* (2006.01)
*A61F 9/00* (2006.01)
*A61B 34/30* (2016.01)
*A61B 34/20* (2016.01)

(52) U.S. Cl.
CPC .......... *A61B 90/14* (2016.02); *A61F 9/00736* (2013.01); *A61F 2009/0035* (2013.01)

(58) Field of Classification Search
CPC . A61F 2090/3945; A61B 90/11; A61B 90/13; A61B 90/14; A61B 90/50; A61B 90/361; A61B 1/0016; A61B 34/20; A61B 34/30; A61B 34/37; A61B 34/76; A61B 2034/305
See application file for complete search history.

(56) References Cited

U.S. PATENT DOCUMENTS

| | | | |
|---|---|---|---|
| 5,598,269 A | 1/1997 | Kitaevich et al. | |
| 6,547,782 B1* | 4/2003 | Taylor | A61B 34/20 606/14 |
| 2013/0123798 A1* | 5/2013 | Tsao | A61B 90/10 606/130 |
| 2014/0194699 A1* | 7/2014 | Roh | A61B 34/30 600/249 |
| 2015/0157468 A1* | 6/2015 | Wakayama | A61B 90/11 606/86 R |
| 2017/0007335 A1* | 1/2017 | Popovic | B25J 9/12 |
| 2020/0246085 A1* | 8/2020 | Noonan | A61B 90/13 |

OTHER PUBLICATIONS

International Search Report and Written Opinion issued in PCT Application No. PCT/US2018/019760 dated Apr. 30, 2018, 7 pages.

* cited by examiner

LASER-ASSISTED SURGICAL ALIGNMENT

CROSS-REFERENCE TO RELATED APPLICATION

This application claims the benefit of U.S. Provisional Application No. 62/464,297, filed Feb. 27, 2017, the contents of which are incorporated herein by reference in their entirety.

STATEMENT REGARDING FEDERALLY SPONSORED RESEARCH OR DEVELOPMENT

This invention was made with Government support under EY024065 awarded by the National Institutes of Health. The Government has certain rights in the invention.

TECHNICAL FIELD

This disclosure generally relates to a robotic surgical system and, more particularly, laser-assisted alignment in such a robotic surgical system.

BACKGROUND

Since the advent of robot-assisted surgery, the value of using robotic systems to assist in surgical procedures in the modern operating theater has been demonstrated. However, most intraocular surgical procedures continue to be manually performed by surgeons. One of the most common procedures is cataract surgery, which is performed about 2.5 million times a year in the United States alone. With the use of femtosecond lasers, laser-based technologies have allowed autonomous completion of specific procedures of cataract surgery, including capsulorhexis and lens fragmentation. While effective in performing such procedures, laser-based technologies are generally unable to perform surgical procedures involving physical manipulation such as removal of an emulsified lens or insertion of an intraocular lens implant.

It is against this background that a need arose to develop the embodiments described herein.

SUMMARY

In some embodiments, a robotic surgery system includes: (1) a positioning stage and (2) at least one manipulator arm mounted to the positioning stage, wherein the manipulator arm includes a track and a tool carriage moveably mounted to the track, and the tool carriage includes a base and a pair of light emitting devices mounted to the base.

In some embodiments, a laser-assisted alignment method includes: (1) providing a robotic manipulator including a first laser and a second laser, wherein an optical axis of the first laser and an optical axis of the second laser intersect at a remote center of motion of the robotic manipulator; (2) assigning a location of a target site on a surface; (3) moving the robotic manipulator such that a first laser spot emitted by the first laser is incident on the target site on the surface; and (4) moving the robotic manipulator such that a second laser spot emitted by the second laser is incident on the first laser spot on the surface.

Other aspects and embodiments of this disclosure are also contemplated. The foregoing summary and the following detailed description are not meant to restrict this disclosure to any particular embodiment but are merely meant to describe some embodiments of this disclosure.

BRIEF DESCRIPTION OF THE DRAWINGS

For a better understanding of the nature and objects of some embodiments of this disclosure, reference should be made to the following detailed description taken in conjunction with the accompanying drawings.

DETAILED DESCRIPTION

Laser-Assisted Surgical Alignment

Embodiments of this disclosure relate to laser-assisted alignment in a robotic surgical system, such as one used to perform intraocular surgical procedures. In some embodiments, a set of lasers are included to visualize and align a remote center of motion (RCM) of a surgical robotic manipulator to an incision site (or other target site).

To reduce stress at an entry site during surgery, a surgical tool should be constrained about its incision site, such as in the eye for intraocular surgery. This incision site should be substantially coincident with a pivot point of the surgical tool for a duration of a surgical procedure. If this condition is not satisfied, then self-sealing properties of a surrounding tissue (e.g., corneal tissue) may be diminished, resulting in post-operative complications (e.g., corneal incision leakage). This clinical criterion specifies the use of a mechanical RCM for a robotic surgical system.

In some embodiments, a robotic surgical system includes at least one surgical robotic manipulator that is configured to constrain motion of a surgical tool mounted to the surgical manipulator such that an axis of the surgical tool extends through an RCM while remaining in a planar region specified based on a rotational orientation of the surgical manipulator. The RCM is capable of three-dimensional translation with respect to a patient for the purpose of aligning the RCM of the surgical manipulator to a surgical incision site. In addition, the surgical tool is capable of being actuated over a sufficiently large workspace to position and orientate inside a body part being operated. Three degrees of freedom are included for three-dimensional positioning of a tool tip inside the body part, while a fourth is included for rotating an axial orientation of the tool.

Figure 1:
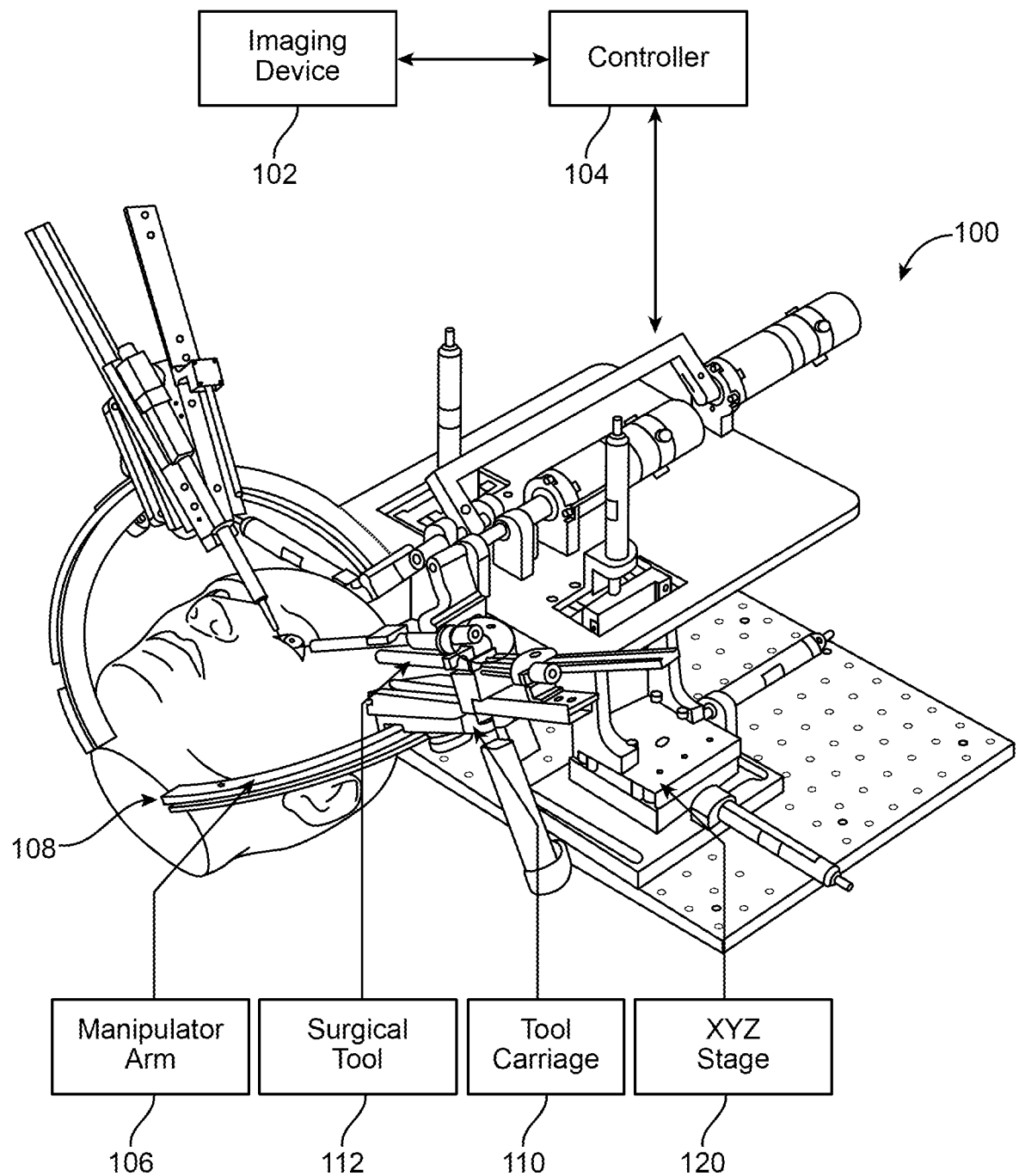
FIG. 1 shows a robotic surgical system according to some embodiments.

FIG. 1 shows a robotic surgical system according to some embodiments. The system includes a surgical manipulator 100, an imaging device 102, and a controller 104. The imaging device 102 can include a surgical microscope (e.g., a stereoscopic ophthalmic microscope), a camera, or both. The controller 104 is connected to the surgical manipulator 100 and the imaging device 102, and directs operation of the surgical manipulator 100 and the imaging device 102.

As shown in FIG. 1, the surgical manipulator 100 includes a pair of independently controllable manipulator arms 106, each including a semi-circular track 108 to which a tool carriage 110 is moveably mounted, and where the tool carriage 110 holds one or more surgical tools 112 that are moveably mounted to the tool carriage 110. Each surgical tool 112 is mechanically constrained about an RCM of the manipulator arm 106 to which the surgical tool 112 is mounted. Examples of the surgical tool 112 include a viscoelastic syringe, an irrigating needle, an infusion-aspiration probe, a light pipe, a vitreous cutter, a cannula, and other microsurgical instruments. Robotic motion of various components of the manipulator arms 106 is driven by actuators, such as motors and associated drive electronics, as directed by the controller 104.

The pair of manipulator arms 106 allow multiple surgical tools 112 to operate independently from each other, but have respective RCMs that are simultaneously enforced and in close proximity to each other (e.g., about 12 mm or less, or about 10 mm to about 12 mm). The four degrees of freedom (per tool 112) are (1, 2) rotations about two different, substantially orthogonal axes which intersect at the RCM, (3) translation in and out of a body part being operated along a tool axis or centerline, and (4) rotation about the tool axis. In addition, each tool 112 can be actuated to translate a position of its RCM relative to a patient for the purpose of aligning to a surgical incision site. Although the two manipulator arms 106 are shown in the FIG. 1, more than two or a single one of such manipulator arms 106 can be included in other embodiments.

Figure 2:
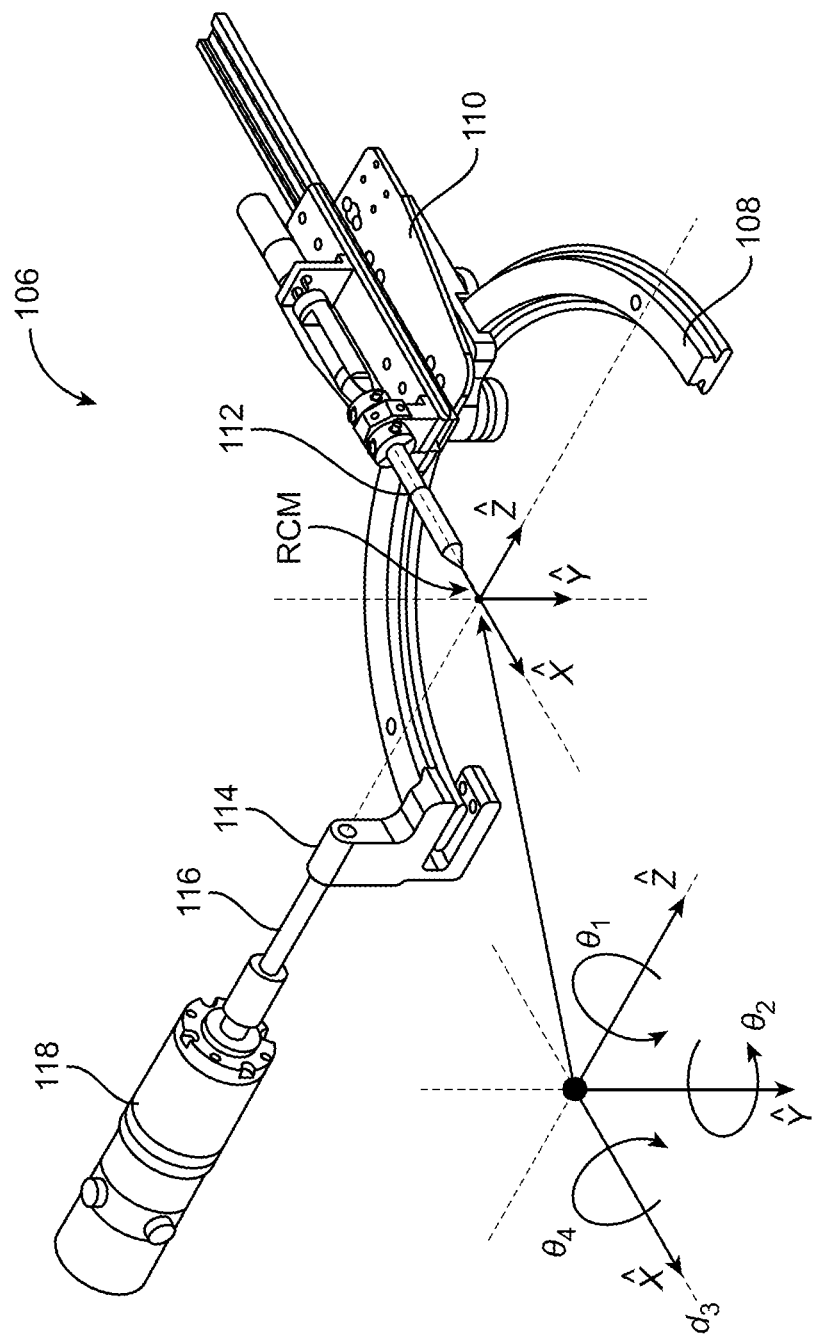
FIG. 2 shows a manipulator arm included in a robotic surgical system according to some embodiments.

A single one of the manipulator arms 106 is shown in FIG. 2, according to some embodiments. Additional manipulator arms 106 can be similarly configured as explained below. The RCM of the manipulator arm 106 is mechanically enforced by mounting the surgical tool 112 to the tool carriage 110 that is slidable along the semi-circular track 108, allowing rotation about $Y^\wedge$ by $\theta_2$. The semi-circular track 108 is mounted to a rotational joint 114, which allows rotation about $Z^\wedge$ by $\theta_1$. The semi-circular track 108 and the rotational joint 114 are aligned such that their rotational axes are substantially orthogonal and intersect at the RCM. The surgical tool 112 is mounted such that its axis or centerline intersects the axis of rotation of the semi-circular track 108 and passes through the RCM. In this way, in-and-out translational motion of the tool 112 is denoted as $d_3$, and rotation of the tool 112 about its centerline is denoted as $\theta_4$. The semi-circular track 108 is mounted, via the rotational joint 114, to a rotational shaft 116 that is driven to rotate by an actuator 118, such as a motor and associated drive electronics. An axis of rotation of the shaft 116 is substantially coincident with the axis of rotation of the rotational joint 114.

Referring back to FIG. 1, to allow three-dimensional translation of the mechanically constrained RCMs, the manipulator arms 106 are mounted to a multi-axis positioning stage 120 capable of three-dimensional XYZ translation. Translational motion of the stage 120 is driven by a set of actuators, such as motors and associated drive electronics.

Figure 3:
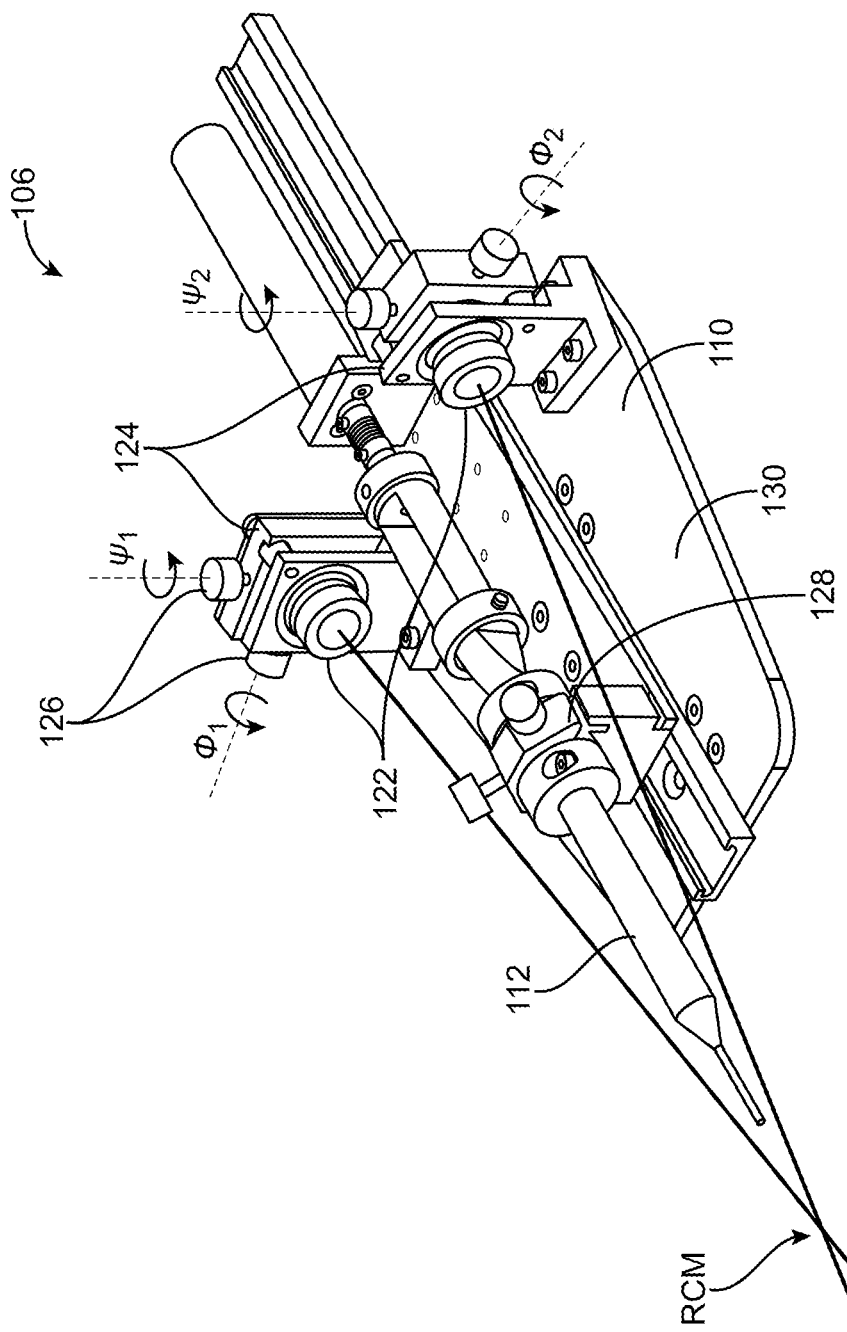
FIG. 3 shows a laser-mounted tool carriage included in a manipulator arm according to some embodiments.

The RCM is an invisible point in space. To allow visualization of the RCM, each of the manipulator arms 106 includes a pair of light emitting devices in the form of a pair of lasers 122, which are mounted to the tool carriage 110, via laser supports 124 that accommodate and secure the lasers 122, to emit light beams (e.g., laser beams) that intersect at the RCM as shown in FIG. 3. As shown in FIG. 3, the tool carriage 110 includes a base 130 and a tool holder 128 mounted to the base 130 to accommodate and secure the surgical tool 112. The lasers 122 are mounted to the base 130 of the tool carriage 110 on opposite sides of the surgical tool 112 and the tool holder 128, and are angled such that the emitted light beams converge at the RCM. When visible light spots (e.g., laser spots) produced by the lasers 122 largely or substantially converge on a surface of a body part to be operated, that convergence point is deemed to be coincident with the mechanical RCM. In this way, aligning the mechanical RCM of the manipulator arm 106 to a surgical incision site can be automatically performed by the controller 104, through integrating control of the stage 120 with computer-vision feedback assisted by images acquired by the imaging device 102. After a surgeon selects the surgical incision site, visual feedback guides the stage 120 to first align one of the light spots to the incision site, and then registers an optical axis of the laser 122 emitting the aligned light spot. By moving the stage 120 along the registered optical axis and searching for a minimal detected area of the light spots on an image, alignment of the RCM to the incision site can be achieved. The alignment procedure can be completed within a relatively short time duration (e.g., less than about two minutes to complete), and can be performed just once per surgery. With the alignment procedure completed, operation of the robotic surgical system can proceed towards surgery, and the surgical tool 112 is translated towards the body part.

Figure 4:
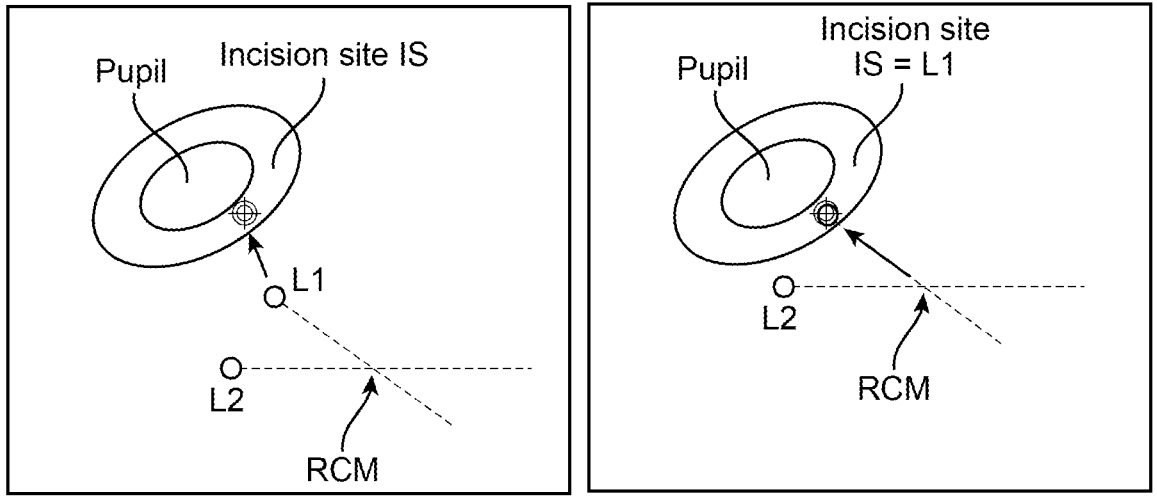
FIG. 4 shows a sequence of operations for laser-assisted alignment of a remote center of motion (RCM) to a surgical incision site, according to some embodiments.

FIG. 4 shows a sequence of operations for laser-assisted alignment of an RCM to a surgical incision site, according to some embodiments. Certain operations of this alignment procedure can be automatically performed (e.g., by the controller 104 shown in FIG. 1), or can be performed under manual control.

Initially, a location of the surgical incision site IS is selected, such as received via input from a surgeon to select a point or an area of an image of a surface of a body part to be operated. Next, a multi-axis positioning stage (e.g., the stage 120 shown in FIG. 1) is moved such that a first laser spot L1 emitted by a first laser is largely or substantially aligned with (or largely or substantially intersects, overlaps, converges, or is coincident with or is incident on) the location of the surgical incision site IS, as represented in an image of the body part. Once the first laser spot L1 is aligned to the surgical incision site IS, an optical axis of the first laser emitting the first laser spot L1 is registered, and further movement of the positioning stage is along the optical axis of the first laser. Next, the positioning stage is moved along the optical axis of the first laser such that a second laser spot L2 emitted by a second laser is largely or substantially aligned with (or largely or substantially intersects, overlaps, converges, or is coincident with or is incident on) a location of the first laser spot L1, and is largely or substantially aligned with (or largely or substantially intersects, overlaps, converges, or is coincident with or is incident on) the location of the surgical incision site IS, as represented in an image of the body part. Sufficient alignment of the first laser spot L1 and the second laser spot L2 can be assessed by, for example, reducing or minimizing a total area of the first laser spot L1 and the second laser spot L2 incident on the surface of the body part, as represented in the image of the body part. At this point, the RCM is deemed to be aligned with the surgical incision site IS.

Referring back to FIG. 3, due to manufacturing tolerances of the lasers 122 (e.g., including a deflection angle of ±10° and a beam offset of ±1 mm), as well as assembly and manufacturing tolerances of components for mounting the lasers 122 to the tool carriage 110, the manipulator arm 106 includes a post-mounting precision adjustment mechanism in each of the laser supports 124, each of which includes two substantially orthogonally mounted thumb screws 126. Each laser 122 is secured in a spherical bearing, and the thumb screws 126—when rotated to tighten—push against a housing of the laser 122, thereby changing a pitch angle $\varphi_1$ (or $\varphi_2$) and a yaw angle $\psi_1$ (or $\psi_2$) of an emitted laser beam about two different, substantially orthogonal axes. Compression springs are included to provide a return motion.

Laser beams emitted by the lasers 122 can be independently aligned to pass through the RCM by a calibration procedure. First, a flat precision-ground plate is mounted substantially orthogonal to a fixed base of the robotic surgery system and positioned such that its surface is aligned with the $\hat{Z}$ axis (see FIG. 2). The tool carriage 110 is then repeatedly cycled through its $\theta_2$ rotation, and the laser yaw angle $\psi_1$ (or $\psi_2$) is adjusted until the rotational motion repeatedly produced a substantially stationary laser spot on the flat plate. Once attained, the angular deflection in $\psi_1$ (or $\psi_2$) is deemed to be addressed. Second, the flat plate is moved along its normal direction (along $\hat{X}$), and the laser pitch angle $\varphi_1$ (or $\varphi_2$) is adjusted such that the laser spot remains substantially stationary as the plate is moved, thereby addressing the angular deflection in $\varphi_1$ (or $\varphi_2$). Once complete, the calibration procedure is performed on the other laser 122. After the calibration procedure is completed for both of the lasers 122, the lasers 122 are deemed to be aligned to intersect at the RCM, which can be confirmed by actuating a tool tip through the RCM and noting the laser deflection.

Embodiments of the laser-assisted alignment procedure can be applied in a variety of robotic surgery systems, including intraocular robotic surgery systems, as well as other applications that involve minimally invasive surgeries or alignment of an RCM. A comparative approach for alignment involves accurately calibrating and positioning a tool at an RCM, and subsequent re-alignment of a tip of that tool to an incision site. This procedure involves physical contact between the tool and a patient during alignment. On the other hand, the laser-assisted alignment procedure of some embodiments is a non-contact approach. A one-time calibration can be performed on lasers themselves, and, even if a resolution of a surgical tool itself is constrained, an accurate alignment of that tool to an incision site can be achieved.

Controller

Figure 5:
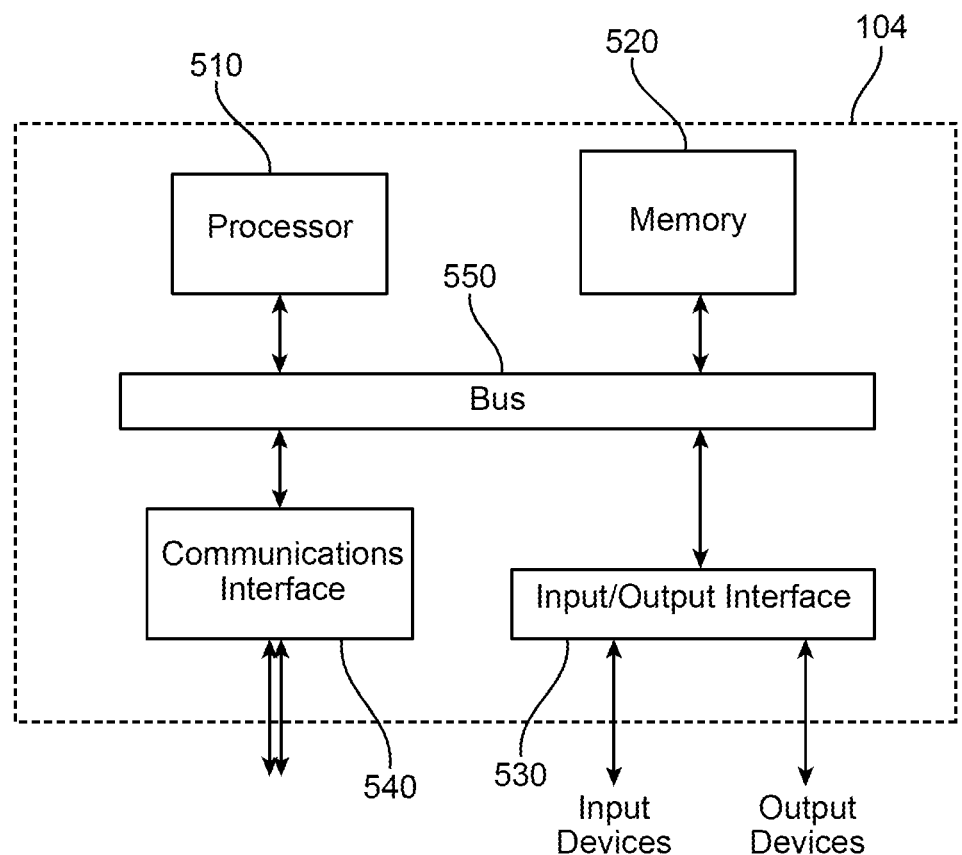
FIG. 5 shows a controller included in a robotic surgical system according to some embodiments.

FIG. 5 shows the controller 104 (or other computing device) according to some embodiments. The controller 104 includes a processor 510, a memory 520, an input/output interface 530, and a communications interface 540. A bus 550 provides a communication path between two or more of the components of controller 104. The components shown are provided by way of example and are not limiting. The controller 104 can have additional or fewer components, or multiple of the same component.

The processor 510 represents one or more of a microprocessor, microcontroller, an application-specific integrated circuit (ASIC), and a field-programmable gate array (FPGA), along with associated logic.

The memory 520 represents one or both of volatile and non-volatile memory for storing information. Examples include semiconductor memory devices such as erasable programmable read-only memory (EPROM), electrically erasable programmable read-only memory (EEPROM), random-access memory (RAM), and flash memory devices, discs such as internal hard drives, removable hard drives, magneto-optical, compact disc (CD), digital versatile disc (DVD), and Blu-ray discs, memory sticks, and the like.

The functionality of the robotic surgical system of some embodiments can be implemented as processor-executable instructions in the memory 520, executed by the processor 510.

The input/output interface 530 represents electrical components and optional instructions that together provide an interface from the internal components of the controller 104 to external components. Examples include a driver integrated circuit with associated programming.

The communications interface 540 represents electrical components and optional instructions that together provide an interface from the internal components of the controller 104 to external networks.

The bus 550 represents one or more connections between components within the controller 104. For example, the bus 550 may include a dedicated connection between the processor 510 and memory 520 as well as a shared connection between the processor 510 and multiple other components of the controller 104.

Example Embodiments

In an aspect according to some embodiments, a robotic surgery system includes: (1) a positioning stage and (2) at least one manipulator arm mounted to the positioning stage. The manipulator arm includes a track and a tool carriage moveably mounted to the track, and the tool carriage includes a base and a pair of light emitting devices mounted to the base.

In some embodiments of the robotic surgery system, the pair of light emitting devices are a pair of lasers.

In some embodiments of the robotic surgery system, the pair of light emitting devices are angled such that light beams emitted by the pair of light emitting devices converge or intersect at a remote center of motion of the manipulator arm. In some embodiments, the pair of light emitting devices are angled relative to the base such that optical axes of the pair of light emitting devices converge or intersect at the remote center of motion of the manipulator arm.

In some embodiments of the robotic surgery system, the tool carriage includes a tool holder mounted to the base, and the pair of light emitting devices are mounted to the base on opposite sides of the tool holder. In some embodiments, the tool holder is configured to accommodate and secure a surgical tool, such that an axis of the surgical tool extends through the remote center of motion.

In some embodiments of the robotic surgery system, the tool carriage includes a pair of supports mounted to the base, and the pair of light emitting devices are mounted to the base via respective ones of the pair of supports. In some embodiments, each of the pair of supports includes an adjustment mechanism to change emission angles about two different axes, such as two substantially orthogonal axes.

In some embodiments of the robotic surgery system, the manipulator arm includes a rotational shaft and an actuator mounted to the rotational shaft. The track is mounted to the rotational shaft, and the actuator is configured to rotate the rotational shaft and the track.

In some embodiments of the robotic surgery system, the positioning stage is a multi-axis positioning stage.

In some embodiments of the robotic surgery system, the pair of light emitting devices are a first light emitting device and a second light emitting device, and the robotic surgery system includes a controller connected to the positioning stage and the manipulator arm. In some embodiments, the controller is configured to: (a) receive, as a user input, a location of a surgical incision site on a surface; (b) direct the positioning stage to move such that a first light spot emitted by the first light emitting device is aligned with, or intersects or is incident on, the location of the surgical incision site on the surface; and (c) direct the positioning stage to move such that a second light spot emitted by the second light emitting device is aligned with, or intersects or is incident on, the first light spot on the surface.

In some embodiments of the robotic surgery system, the controller in operation (b) is configured to determine an orientation of an optical axis of the first light emitting device such that the first light spot emitted by the first light emitting device is aligned with, or intersects or is incident on, the location of the surgical incision site, and the controller in operation (c) is configured to direct the positioning stage to move along the optical axis of the first light emitting device.

In some embodiments of the robotic surgery system, the controller in operations (b) and (c) is configured to direct the positioning stage to move based on visual feedback from a set of images acquired of the surface. In some embodiments, the controller is configured to receive, as a visual input, the set of images acquired of the surface, and the controller in operations (b) and (c) is configured to direct the positioning stage to move based on the visual input.

In some embodiments of the robotic surgery system, the controller in operation (c) is configured to determine alignment of the first light spot and the second light spot based on reducing or minimizing a total area of the first light spot and the second light spot incident on the surface, as represented in an image of the surface.

In some embodiments of the robotic surgery system, the robotic surgery system includes an imaging device connected to the controller, and the imaging device is configured to acquire the set of images of the surface.

In another aspect according to some embodiments, a laser-assisted alignment method includes: (1) providing a robotic manipulator including a first laser and a second laser, wherein the first laser emits a first laser beam, the second laser emits a second laser beam, and the first laser beam and the second laser beam intersect at a remote center of motion of the robotic manipulator; (2) assigning a location of a target site on a surface; (3) moving the robotic manipulator such that a first laser spot emitted by the first laser is aligned with, or intersects or is incident on, the location of the target site on the surface; and (4) moving the robotic manipulator such that a second laser spot emitted by the second laser is aligned with, or intersects or is incident on, the first laser spot on the surface.

In some embodiments of the method, the robotic manipulator is configured to constrain motion of a tool mounted to the robotic manipulator such that an axis of the tool extends through the remote center of motion. In some embodiments, an optical axis of the first laser and an optical axis of the second laser intersect at the remote center of motion.

In some embodiments of the method, operation (3) includes determining an orientation of the optical axis of the first laser such that the first laser spot emitted by the first laser is aligned with, or intersects or is incident on, the location of the target site, and operation (4) includes moving the robotic manipulator along the optical axis of the first laser.

In some embodiments of the method, moving the robotic manipulator in operations (3) and (4) is based on visual feedback from a set of images acquired of the surface.

In some embodiments of the method, operation (4) includes determining alignment of the first laser spot and the second laser spot based on reducing or minimizing a total area of the first laser spot and the second laser spot incident on the surface, as represented in an image of the surface.

As used herein, the singular terms "a," "an," and "the" may include plural referents unless the context clearly dictates otherwise. Thus, for example, reference to an object may include multiple objects unless the context clearly dictates otherwise.

As used herein, the term "set" refers to a collection of one or more objects. Thus, for example, a set of objects can include a single object or multiple objects.

As used herein, the terms "connect," "connected," and "connection" refer to an operational coupling or linking. Connected objects can be directly coupled to one another or can be indirectly coupled to one another, such as via one or more other objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, concentrations, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a range of about 1 to about 200 should be understood to include the explicitly recited limits of about 1 and about 200, but also to include individual values such as about 2, about 3, and about 4, and sub-ranges such as about 10 to about 50, about 20 to about 100, and so forth.

While the disclosure has been described with reference to the specific embodiments thereof, it should be understood by those skilled in the art that various changes may be made and equivalents may be substituted without departing from the true spirit and scope of the disclosure as defined by the appended claims. In addition, many modifications may be made to adapt a particular situation, material, composition of matter, method, operation or operations, to the objective, spirit and scope of the disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations are not a limitation of the disclosure.

What is claimed is:

1. A robotic surgery system comprising:
a positioning stage; and
at least one manipulator arm mounted to the positioning stage,
wherein the manipulator arm includes a track and a tool carriage moveably mounted to the track, and wherein the tool carriage includes:
a base,
a pair of light emitting devices mounted to the base, and
a tool holder configured to secure a surgical tool to the base in a fixed and calibrated position together with the pair of light emitting devices.

2. The robotic surgery system of claim 1, wherein the pair of light emitting devices are a pair of lasers.

3. The robotic surgery system of claim 1, wherein the pair of light emitting devices are angled relative to the base such that optical axes of the pair of light emitting devices intersect at a remote center of motion of the manipulator arm.

4. The robotic surgery system of claim 3, wherein the tool holder is mounted to the base, and the pair of light emitting devices are mounted to the base on opposite sides of the tool holder.

5. The robotic surgery system of claim 4, wherein the tool holder is configured to secure the surgical tool, such that an axis of the surgical tool extends through the remote center of motion.

6. A robotic surgery system comprising:
a positioning stage; and
at least one manipulator arm mounted to the positioning stage,
wherein the manipulator arm includes a track and a tool carriage moveably mounted to the track, and
wherein the tool carriage includes:
a base,
a pair of light emitting devices mounted to the base,
a tool holder mounted to the base, wherein the pair of light emitting devices are mounted to the base on opposite sides of the tool holder, and
a pair of supports mounted to the base,
wherein the pair of light emitting devices are mounted to the base via respective ones of the pair of supports, and
wherein the pair of light emitting devices are angled relative to the base such that optical axes of the pair of light emitting devices intersect at a remote center of motion of the manipulator arm, and
wherein the tool holder is configured to secure the surgical tool, such that an axis of the surgical tool extends through the remote center of motion.

7. The robotic surgery system of claim 6, wherein each of the pair of supports includes an adjustment mechanism to change emission angles about two different axes.

8. The robotic surgery system of claim 1, wherein the pair of light emitting devices are a first light emitting device and a second light emitting device, the robotic surgery system further comprises a controller connected to the positioning stage, and the controller is configured to:
(a) receive, as an input, a location of a surgical incision site on a surface;
(b) direct the positioning stage to move such that a first light spot emitted by the first light emitting device is aligned with the surgical incision site on the surface; and
(c) direct the positioning stage to move such that a second light spot emitted by the second light emitting device is aligned with the first light spot on the surface.

9. The robotic surgery system of claim 8, wherein the controller in (b) is configured to determine an orientation of an optical axis of the first light emitting device such that the first light spot emitted by the first light emitting device is aligned with the surgical incision site, and the controller in (c) is configured to direct the positioning stage to move along the optical axis of the first light emitting device.

10. The robotic surgery system of claim 8, wherein the controller is configured to direct the positioning stage to move based on visual feedback from a set of images acquired of the surface.

11. The robotic surgery system of claim 8, wherein the controller in (c) is configured to determine alignment of the first light spot and the second light spot based on reducing a total area of the first light spot and the second light spot incident on the surface.

12. A laser-assisted alignment method comprising:
(1) providing a robotic manipulator including a first laser and a second laser, wherein an optical axis of the first laser and an optical axis of the second laser intersect at a remote center of motion of the robotic manipulator;
(2) assigning a location of a target site on a surface in a first step;
(3) moving the robotic manipulator in a second step subsequent to the first step such that a first laser spot emitted by the first laser is incident on the target site on the surface that was assigned in the first step; and
(4) moving the robotic manipulator in a third step subsequent to the second step such that a second laser spot emitted by the second laser is incident on the first laser spot on the surface that was emitted in the second step.

13. The method of claim 12, wherein the robotic manipulator is configured to constrain motion of a tool mounted to the robotic manipulator such that an axis of the tool extends through the remote center of motion.

14. The method of claim 12, wherein moving the robotic manipulator in (3) includes determining an orientation of the optical axis of the first laser such that the first laser spot emitted by the first laser is incident on the target site, and moving the robotic manipulator in (4) includes moving the robotic manipulator along the optical axis of the first laser.

15. The method of claim 12, wherein moving the robotic manipulator in (4) includes determining alignment of the first laser spot and the second laser spot based on reducing a total area of the first laser spot and the second laser spot incident on the surface.

* * * * *

UNITED STATES PATENT AND TRADEMARK OFFICE
CERTIFICATE OF CORRECTION

PATENT NO. : 11,564,757 B2
APPLICATION NO. : 16/487074
DATED : January 31, 2023
INVENTOR(S) : Tsu-Chin Tsao et al.

Page 1 of 1

It is certified that error appears in the above-identified patent and that said Letters Patent is hereby corrected as shown below:

In the Specification

Column 1, Line 14, after the sub-title "STATEMENT REGARDING FEDERALLY SPONSORED RESEARCH OR DEVELOPMENT", please replace the paragraph with the following paragraph: This invention was made with Government support under EY024065 awarded by the National Institutes of Health. The Government has certain rights in the invention.

Signed and Sealed this
Eighteenth Day of April, 2023

Katherine Kelly Vidal
*Director of the United States Patent and Trademark Office*